US00PP31752P3

(12) United States Plant Patent

Lewis et al.

(10) Patent No.: US PP31,752 P3
(45) Date of Patent: May 12, 2020

(54) *CANNABIS* PLANT NAMED 'CAKE BATTER COOKIES'

(50) Latin Name: ***Cannabis* hybrid**
Varietal Denomination: CAKE BATTER COOKIES

(71) Applicant: Biotech Institute LLC, Westlake Village, CA (US)

(72) Inventors: Mark A. Lewis, Westlake Village, CA (US); Steven Haba, Westlake Village, CA (US)

(73) Assignee: Biotech Institute, LLC, Westlake Village, CA (US)

( * ) Notice: Subject to any disclaimer, the term of this patent is extended or adjusted under 35 U.S.C. 154(b) by 0 days.

(21) Appl. No.: 15/998,287

(22) Filed: Aug. 1, 2018

(65) Prior Publication Data

US 2019/0183004 P1 Jun. 13, 2019

Related U.S. Application Data

(60) Provisional application No. 62/596,561, filed on Dec. 8, 2017.

(51) Int. Cl.
*A01H 5/02* (2018.01)
*A01H 6/28* (2018.01)
*A61K 36/185* (2006.01)

(52) U.S. Cl.
USPC ..... Plt./258
CPC ..... *A01H 6/28* (2018.05); *A61K 36/185* (2013.01)

(58) Field of Classification Search
USPC ..... Plt./258, 263.1
CPC ... A01H 5/12; A01H 5/00; A01H 5/02; A01H 6/28; A61K 36/185
See application file for complete search history.

(56) References Cited

U.S. PATENT DOCUMENTS

| | | | |
|---|---|---|---|
| 9,095,554 | B2 | 8/2015 | Lewis et al. |
| 9,370,164 | B2 | 6/2016 | Lewis et al. |
| PP27,475 | P2 | 12/2016 | Kubby |
| 9,642,317 | B2 | 5/2017 | Lewis et al. |
| 2014/0287068 | A1 | 9/2014 | Lewis et al. |
| 2014/0298511 | A1 | 10/2014 | Lewis et al. |
| 2015/0359188 | A1 | 12/2015 | Lewis et al. |
| 2015/0366154 | A1 | 12/2015 | Lewis et al. |
| 2016/0324091 | A1 | 11/2016 | Lewis et al. |
| 2017/0202170 | A1 | 7/2017 | Lewis et al. |
| 2018/0064055 | A1 | 3/2018 | Lewis et al. |
| 2018/0143212 | A1 | 5/2018 | Lewis et al. |

FOREIGN PATENT DOCUMENTS

| | | | |
|---|---|---|---|
| WO | WO 2014/145490 | A2 | 9/2014 |
| WO | WO 2015/065544 | A1 | 5/2015 |
| WO | WO 2016/105514 | A1 | 6/2016 |
| WO | WO 2016/123160 | A1 | 8/2016 |
| WO | WO 2018/094359 | A1 | 5/2018 |

OTHER PUBLICATIONS

Reddit 2016 Cake batter?, retrieved on Jun. 10, 2019, retrieved from the Internet at https://www.reddit.com/r/CannabisExtracts/comments/4jcow1/cake_batter/, 5 pp. (Year: 2016).*
Weed Connection 2016 #CakeBatter #OG, retrieved on Jun. 11, 2019, retrieved from the Internet at https://weedconnection.com/medz/link/cakebatterogkush.html, 2 pp. (Year: 2016).*

* cited by examiner

*Primary Examiner* — June Hwu
(74) *Attorney, Agent, or Firm* — Cooley LLP

(57) ABSTRACT

The present invention provides a new and distinct *cannabis* cultivar designated as 'CAKE BATTER COOKIES'. Disclosed herein are main terpenes of 'CAKE BATTER COOKIES', which are limonene, beta-caryophyllene, beta-pinene, linalool, alpha-humulene, alpha-pinene, fenchol, myrcene, alpha-bisabolol, and alpha-terpineol. Also, the present invention provides the estimated concentration of the $THC_{max}$, $CBD_{max}$, and $CBG_{max}$, about 6.5-14.21%, about 5.36-9.82%, and about 0.11-0.42%, respectively, at the time of assaying metabolites from flower samples of 'CAKE BATTER COOKIES'.

8 Drawing Sheets

Latin name of genus and species: *Cannabis* hybrid.
Variety denomination: 'CAKE BATTER COOKIES'.

BACKGROUND OF THE INVENTION

The present invention relates to a new and distinct *cannabis* cultivar designated as 'CAKE BATTER COOKIES'.

This new cultivar is the result of controlled-crosses between proprietary cultivars made by the inventors. The new cultivar of 'CAKE BATTER COOKIES' was asexually reproduced via a stem 'cutting' and 'cloning' method by the inventors at Salinas, Calif. Asexual clones from the original source have been tested in greenhouses, nurseries, and/or fields. The properties of each cultivar were found to be transmissible by such asexual reproduction. The cultivar is stable and reproduces true to type in successive generations of asexual reproduction.

TAXONOMY AND NOMENCLATURE

*Cannabis*, more commonly known as marijuana, is a genus of flowering plants that includes at least three species, *Cannabis saliva, Cannabis indica*, and *Cannabis ruderalis* as determined by plant phenotypes and secondary metabolite profiles. In practice however, *cannabis* nomenclature is often used incorrectly or interchangeably. *Cannabis* literature can be found referring to all *cannabis* varieties as "*salivas*" or all cannabinoid producing plants as "*indicas*". Indeed the promiscuous crosses of indoor *cannabis* breeding programs have made it difficult to distinguish varieties, with most *cannabis* being sold in the United States having features of both *sativa* and *indica* species.

Human cultivation history of *Cannabis* dates back 8000 years (Schultes, R E., 1970, Random thoughts and queries on the botany of *Cannabis*. Pages 11-38 in: C R B Joyce, and S H Curry eds., THE BOTANY AND CHEMISTRY OF *CANNABIS*. J. & A. Churchill. London, England). Hemp cloth recovered in Europe dates back 6000 years (Small, E, Beckstead, H D, and Chan, A, 1975, The evolution of cannabinoid phenotypes in *Cannabis*, ECONOMIC BOTANY 29(3):219-232). The written record of the pharmacologic properties of *Cannabis* goes back more than 4000 years (Ti, H. 2737 BC. NEI JING SU WEN HUANG TI, Yellow Emperor's Classic on Internal Medicine; referred to without citation in Small et al. 1975 Supra).

The taxonomy and nomenclature of the highly variable genus *Cannabis* (Emboden, W A, 1974, ECONOMIC BOTANY 28(3):304-310; Small, E and Cronquist, A, 1976, TAXON 25(4):405-435; Small E and Cronquist, A, 1977, TAXON 26(1):110; Hillig, K W and Mahlberg, P G, 2004, American Journal of Botany 91(6):966-975), remains in question. This is in spite of the fact that its formal scientific name, '*Cannabis sativa* L.', assigned by Carolus Linneaus (Linnaeus, C, 1753, SPECIES PLANTARUM 2:1027, Salvius, Stockholm, Facsimile edition, 1957-1959, Ray Society, London, U.K.), is one of the oldest established names in botanical history and is still accepted to this day. Another species in the genus, '*Cannabis indica* Lam.' was formally named somewhat later (de Lamarck, J B, 1785, ENCYCLOPEDIE METHODIQUE DE BOTANIQUE, 1(2):694-695), but is still very old in botanical history. In 1785, Jean-Baptiste Lamarck published a description of a second species of *Cannabis*, which he named *Cannabis indica*. Lamarck based his description of the newly named species on plant specimens collected in India. *C. indica* was described as relatively short, conical, and densely branched, whereas *C. saliva* was described as tall and laxly branched (Schultes R. E. et al, 1974, Harvard University Botanical Museum Leaflets, 23:337-367). *C. indica* plants were also described as having short. broad leaflets whereas those of *C. saliva* were characterized as relatively long and narrow (Anderson L. C., 1980, Harvard University Botanical Museum Leaflets, 28:61-69). *C. indica* plants conforming to Schultes' and Anderson's descriptions may have originated from the Hindu Kush mountain range. Because of the often harsh and variable (extremely cold winters, and warm summers) climate of those parts, *C. indica* is well-suited for cultivation in temperate climates.

Three other species names were proposed in the 1800s to distinguish plants with presumably different characteristics (*C. macrosperma* Stokes, *C. chinensis* Delile, *C. gigantean* Vilmorin), none of which are accepted today, although the epithet "*indica*" lives on as a subspecies of *C. sativa* ('*C. sativa* ssp. *indica* Lam.', Small and Cronquist 1976 Supra).

In the 20th century, two new names were added to the liturgy of proposed '*Cannabis* species: *C. ruderalis*' Janischevsky and a hybrid, x'*C. intersita*' Sojak. (Small, E, Jui, P Y, and Lefkovitch, L P, 1976, SYSTEMATIC BOTANY 1(1):67-84; Small and Cronquist 1976 Supra). Further, numerous names have been proposed for horticultural variants of '*Cannabis*' but as of 1976, "very few of these have been validly published as formal taxa under the International Code of Botanical Nomenclature." Small and Cronquist 1976 Supra. Moreover, other recent work continues to focus on higher-order evolutionary relationships of the genus. *Cannabis* has been variously ascribed as belonging to mulberry family (Moraceae) (Engler, H G A, Ulmaceae, Moraceae and Urticaceae, pages 59-118 in: A. Engler and K. Prantl eds., 1889, DIE NATURLICHEN PFLANZENFAMILIEN 3(1). W. Engelmann, Leipzig, Germany; Judd, W S, Sanders, R W, and Donoghue, M J, 1994, HARVARD PAPERS IN BOTANY 5:1-51; Humphries, C J and Blackmore, S, A review of the classification of the Moraceae, pages 267-277 In: Crane and Blackmore 1989 id.); nettle family (Urticaceae) (Berg, C C, Systematics and phylogeny of the Urticales, pages 193-220, in: P. R. Crane and S. Blackmore eds., 1989, EVOLUTION, SYSTEMATIC, AND FOSSIL HISTORY OF THE HAMAMELIDAE, VOL. 2, HIGHER HAMAMELIDAE, Clarendon Press, Oxford, U.K.); and most recently in its own family with hops (Humulus), Cannabaceae, or hemp family (Sytsma, K J, et al, 2002, AMERICAN JOURNAL OF BOTANY 89(9): 1531-1546). While the work of Small and Cronquist 1976 Supra, seemed to effectively confine the genus to a single species with 2 subspecies (*C. sativa* s., *C.* s. *indica*), each with two varieties (*C. s.* s. var. *sativa, C. s.* s. var. *spontanea; C. s.* i. var. *indica, C. s.* i. var. *Kafiristanica*) largely on the basis of chemotaxonomy and interfertility of all forms, more recent work (Sytsma et al. 2002 Supra), proposes a two-species concept, resurrecting the binomial *C. indica* Lam. Since Sytsma et al. (2002) provides no key for discriminating between the species, the dichotomous key of Small and Cronquist (1976), which accounts for all forms in nature, whether wild or domesticated, is preferred to classify the characteristics of the plants.

BRIEF SUMMARY OF THE INVENTION

This invention relates to a new and distinctive *cannabis* cultivar designated as 'CAKE BATTER COOKIES'.

The objective of the breeding program which produced novel plants disclosed herein was primarily to develop a *cannabis* cultivar with its unique blend of various cannabinoids and/or terpenes for (a) medicinal effects such as improving appetite and reducing nausea, vomiting and/or chronic pain, as well as neurological and cardiovascular effects, (b) psychoactive effects such as increased motivation and energetic behavior rather than indifference, passiveness and lethargy, and (c) recreational effects with enhanced enjoyment such as food and aroma.

As used herein, the term "cultivar" is used interchangeably with "variety", "strain", and/or "clone".

*Cannabis* plants produce a unique family of terpenophenolic compounds. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. The *cannabis* plant has at least 545 distinct compounds that span 20 chemical classes including cannabinoids, terpenes, terpenoids, amino acids, nitrogenous compounds, simple alcohols, aldehydes, ketones, esters, lactones, acids, fatty acids, steroids, non-cannabinoid phenols, pigments, flavonoids, vitamins, proteins, enzymes, glycoproteins. and hydrocarbons. Terpenes and/or cannabinoids, in particular, have shown great potential in terms of medicinal value.

Terpenes and/or cannabinoids have been shown to be largely responsible for beneficial effects of a *cannabis* plant. In fact, each *cannabis* plant has the varying concentrations of medically viable compounds depending on different strains (genotypes) and their resulting chemotypes. Even a small variation in terpene and/or cannabinoid concentration can cause noticeable differences in the entourage and/or synergistic effects of a *cannabis* plant, which distinguishes one variety from another. Research shows that it relies heavily on the physiological effects produced by terpenes and/or cannabinoids.

Over 100 different kinds of terpenes have been identified in *cannabis* plants although not being as well-studied as cannabinoids, they are instrumental in giving rise to the physiological and psychoactive effects in *cannabis*.

Terpenes are a large and diverse class of organic compounds, produced by a variety of plants. They are often strong smelling and thus may have had a protective function. Terpenes are an important component, not only influencing taste and smell of each *cannabis* strain but also influencing its effects on the mind and body of a subject such as humans and animals. Terpenes are a classification of organic molecules that are found in a wide variety of plants and animals. These molecules are known for their characteristic scents and flavors. The varying terpene concentrations found in *cannabis* plants directly influence the resulting taste and smell, as well as the observed effects. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids. The main terpenes found in *cannabis* plants include, but are not limited to, myrcene, limonene, caryophyllene, pinene, terpinene, terpinolene, camphene, terpineol, phellandrene, carene, humulene, pulegone, sabinene, geraniol, linalool, fenchol, borncol, cucalyptol, and neiolidul.

Cannabinoids are the most studied group of the main physiologically active secondary metabolites in *cannabis*. The classical cannabinoids are concentrated in a viscous resin produced in structures known as glandular trichomes. At least 113 different cannabinoids have been isolated from *cannabis* plants. The main classes of cannabinoids from *cannabis* include tetrahydrocannabinol (THC), cannabidiol (CBD), cannabigerol (CBG), and cannabinol (CBN). Cannabinoid can be at least one of a group comprising tetrahydrocannabinol (THC), cannabidiol (CBD), cannabigerol (CBG), cannabinol (CBN) cannabichromene (CBC), cannabinodiol (CBDL), cannabicyclol (CBL), cannabivarin (CBV), tetrahydrocannabivarin (THCV), cannabidivarin (CBDV), cannabigerovarin (CBGV), cannabichromevarin (CBCV), cannabigerol monomethyl ether (CBGM), cannabielsoin (CBE), cannabicitran (CBT), cannabinol propyl variant (CBNV), cannabitriol (CBO), tetrahydrocannabinolic acid (THCA), tetrahydrocannabivarinic acid (THCVA), cannabidiolic acid (CBDA), cannabigerolic acid (CBGA) and cannabinerolic acid.

Most cannabinoids exist in two forms, as acids and in neutral (decarboxylated) forms. The acidic form of cannabinoids is designated by an "A" at the end of its acronym (i.e. THCA). The cannabinoids in their acidic forms (those ending in "-A") can be converted to their non-acidic forms through a process called decarboxylation when the sample is heated. The phytocannabinoids are synthesized in the plant as acidic forms. While some decarboxylation does occur in the plant, it increases significantly post-harvest and the kinetics increase at high temperatures (Flores-Sanchez and Verpoorte, 2008, Plant Cell Physiol. 49(12): 1767-1782). The biologically active forms for human consumption are the neutral forms. Decarboxylation is usually achieved by thorough drying of the plant material followed by heating it, often by combustion, vaporization, heating, or baking in an oven. Unless otherwise noted, references to cannabinoids in a plant include both the acidic and decarboxylated versions (e.g., CBD and CBDA).

The molecules lose mass through the process of decarboxylation. In order to find the total theoretical active cannabinoids, the acid forms should be multiplied by 87.7%. For example, THCA can be converted to active THC using the formula: THCA×0.877=THC. The maximum THC for the sample is: $THC_{max}$=(THCA×0.877)+THC. This method has been validated according to the principles of the International Conference on Harmonization. Similarly, CBDA can be converted to active CBD and the yield is determined using the yield formula: CBDA×0.877=CBD. Also the maximum amount of CBD yielded, i.e. max CBD for the sample is: $CBD_{max}$=(CBDA×0.877)+CBD. Additionally, CBGA can be converted to active CBG by multiplying 87.8% to CBGA. Thus, the maximum amount of CBG is: $CBG_{max}$=(CBGA×0.878)+CBG.

The biologically active chemicals found in plants, phytochemicals, may affect the normal structure or function of the human body and in some cases treat disease. The mechanisms for the medicinal and psychoactive properties of a *cannabis* plant, like any medicinal herb, produce the pharmacologic effects of its phytochemicals, and the key phytochemicals for a medical *cannabis* plant are cannabinoids and terpenes.

Δ9-Tetrahydrocannabinol (THC) is a psychoactive cannabinoid responsible for many of the effects such as mild to moderate pain relief, relaxation, insomnia and appetite stimulation. THC has been demonstrated to have antidepressant effects. The majority of strains range from 12-21% THC with very potent and carefully prepared strains reaching even higher. While Δ9-Tetrahydrocannabinol (THC) is also implicated in the treatment of disease, the psychotropic activity of THC makes it undesirable for some patients and/or indications.

Tetrahydrocannabinol, THC, is the primary psychoactive and medicinal cannabinoid and is the result of the decarboxylation of tetrahydrocannabinolic acid (THCA), its acidic precursor. THCA, (6ar,10ar)-1-hydroxy-6,6,9-trimethyl-3-pentyl-6a,7,8,10a-tetrahydro-6h-benzochromene-2-carboxylic acid, is found in the trichomes of the plant and converted into THC, which actually exists in only minute quantities in the living plant, after harvest and drying.

Cannabidiol (CBD) is one of the principal cannabinoids found in a *cannabis* plant and is largely considered to be the most medically significant. CBD occurs in many strains, at low levels, <1%. In some cases, CBD can be the dominant cannabinoid, as high as 15% by weight. CBD is non-psychoactive, meaning that unlike THC, CBD does not cause a noticeable "high". CBD has shown potential for medical properties in the treatment of a wide variety of diseases and symptoms, including cancer, nausea, chronic pain, spasms, seizures/epilepsy, anxiety, psoriasis, Crohn's disease, rheumatoid arthritis, diabetes, schizophrenia, post-traumatic stress disorder (PTSD), alcoholism, strokes, multiple sclerosis, and cardiovascular disease. CBD also has been reported to act as a muscle relaxant, antibiotic, anti-inflammatory, and bone stimulant, as well as to improve blood circulation, cause drowsiness, and protect the nervous system. It can provide relief for chronic pain due to muscle spasticity, convulsions and inflammation, as well as effective relief from anxiety-related disorders. It can offer relief for patients with Multiple Sclerosis (MS), Fibromyalgia and Epilepsy. CBD has also been shown to inhibit cancer cell growth when injected into breast and brain tumors in combination with THC.

A *cannabis* cultivar can be used to achieve the desire of patients to be treated with CBD without the adverse side-effects (e.g., psychoactivity) of THC.

Cannabichromene (CBC) is a rare, non-psychoactive cannabinoid, usually found at low levels (<1%) when present. It has been shown to have anti-depressant effects and to improve the pain-relieving effects of THC. Studies have demonstrated that CBC has sedative effects such as promoting relaxation.

Cannabidiol (CBD) and cannabichromene (CBC) are both non-psychoactive and end products of CBG metabolism, like THC, so that they can be used medically.

le;.5qCannabigerol (CBG) is a non-psychoactive cannabinoid. CBG-acid is the precursor to both THC-acid and CBD-acid in the plant usually found at low levels (<1%) when present. It has been demonstrated to have both pain relieving and inflammation reducing effects. CBG reduces intraocular pressure, associated with glaucoma. CBG has been shown to have antibiotic properties and to inhibit platelet aggregation, which slows the rate of blood clotting. While Cannabigerol (CBG), is not considered psychoactive, it is known to block the psychoactive effects of THC and is considered medically active in a variety of conditions. Its precursor, cannabigerolic acid, CBGA, (E)-3-(3,7-Dimethyl-2,6-octadienyl)-2,4-dihydroxy-6-pentylbenzoic acid, is being studied medically.

Cannabinol (CBN) is an oxidative degradation product of THC. It may result from improper storage or curing and extensive processing, such as when making concentrates. It is usually formed when THC is exposed to UV light and oxygen over time. CBN has some psychoactive properties, less strength than THC. CBN is thought to enhance the dizziness and disorientation that users of *cannabis* may experience. It may cause feelings of grogginess, but has been shown to reduce heart rate.

High potency *cannabis* plants contain large quantities of specific terpenes as well as various assortments of other terpenes. For instance, a *cannabis* plant may have a profile with either a high level of, a moderate amount of, or a small amount of various terpenes depending on its cultivar and environmental conditions.

Various cultivars of '*Cannabis*' species have been cultivated in an effort to create a cultivar best suited to meet the interest of inventors according to their own need. The particular plant disclosed herein was discovered in the area where the inventors were intentionally cross-pollinating and cultivating plants described below using standard Mendelian breeding procedures well known to those of ordinary skill in the art. This resulted in the progenies of the inventors' crosses.

The progenies resulting from any selection stage of either the crossing, selfing or backcrossing versions of the breeding regimes of the present invention were asexually reproduced to fix and maintain the desirable THC content, CBs content, terpenes content, the aroma and flavor(s) typical of the desired class, and the other desirable phenotypic and/or genotypic characteristics. The resultant selected *cannabis* cultivar is designated as 'CAKE BATTER COOKIES' disclosed herein.

The inventors reproduced progenies asexually by stem cutting and cloning. This is the origin of this remarkable new cultivar. The plant has been and continues to be asexually reproduced by stem cutting and cloning at the inventors' greenhouses, nurseries and/or fields in Salinas, Calif., Oakland, Calif., and/or Washington, D.C.

The following are the most outstanding and distinguishing chemical characteristics of this new cultivar when grown under normal conditions in Salinas, Calif. Chemical analyses of the new *cannabis* variety and the check variety (or the parental varieties) disclosed herein were performed using standard chemical separation techniques well known to those skilled in the art. Samples for assaying were obtained from flower tissues of the *cannabis* plant disclosed herein. Cannabinoid composition of this cultivar can be determined by assaying the concentration of at least one cannabinoid in a subset (e.g., sample) of the harvested product.

Table 1 includes detailed information of the *cannabis* plant named 'CAKE BATTER COOKIES' including the concentration ranges of terpenes and cannabinoids as tested on flowers sampled on at least four different dates. The *cannabis* plant has been tested in a laboratory setting and/or facility to determine cannabinoids and terpenes concentrations in the *cannabis* plant named 'CAKE BATTER COOKIES' according to the procedures provided in Giese et al. (Journal of AOAC International (2015) 98(6):1503-1522).

1) The main terpenes found in 'CAKE BATTER COOKIES' are limonene, beta-caryophyllene, beta-pinene, linalool, alpha-humulene, alpha-pinene, fenchol, myrcene, alpha-bisabolol, and alpha-terpineol; and
2) The estimated concentration of the total $THC_{max}$, $CBD_{max}$, and $CBG_{max}$ is about 6.50-14.21%, about 5.36-9.82%, and about 0.11-0.42%, respectively, at the time of assaying metabolites from flower samples of 'CAKE BATTER COOKIES'.

Terpene and cannabinoid profiles of 'CAKE BATTER COOKIES' demonstrate that 'CAKE BATTER COOKIES' has a phenotypically unique profile, particular insofar as to the level of terpenes and cannabinoids. This data is presented in tabular form in Table 1.

TABLE 1

| Ranges of Active Cannabinoids and Terpenes | | | | | |
|---|---|---|---|---|---|
| Ranges of Active Cannabinoids (Vo by weight) | | | | | |
| Max THC | 6.50-14.21% | Max CBD | 5.36-9.82% | Max CBG | 0.11-0.42% |
| Ranges of Terpenes (% by weight) | | | | | |
| thujene | 0.00% | gamma-terpinene | 0.00% | hexyl hexanoate | 0.00-0.03% |
| alpha-pinene | 0.07-0.14% | linalool oxide | 0.00-0.04% | octyl butyrate | 0.00-0.03% |
| camphene | 0.01-0.03% | terpinolene | 0.00-0.02% | beta-caryophyllene | 0.16-0.33% |
| sabinene | 0.00% | fenchone | 0.00-0.02% | alpha-humulene | 0.09-0.17% |
| beta-pinene | 0.09-0.18% | linalool | 0.01-0.18% | cis-nerolidol | 0.02-0.04% |
| myrcene | 0.03-0.09% | fenchol | 0.05-0.10% | trans-nerolidol | 0.02-0.04% |
| alpha-phellandrene | 0.00% | — | — | caryophyllene oxide | 0.02-0.03% |

TABLE 1-continued

| Ranges of Active Cannabinoids and Terpenes | | | | | |
|---|---|---|---|---|---|
| carene | 0.00% | camphor | 0.00-0.02% | alpha-bisabolol | 0.04-0.07% |
| alpha-terpinene | 0.00% | isoborneol | 0.00% | nerol | 0.00% |
| limonene | 0.48-1.02% | (−) borneol | 0.01-0.02% | geraniol | 0.00% |
| beta-phellandrene | 0.00% | menthol | 0.00-0.02% | geranyl-acetate | 0.00% |
| cineole | 0.00% | hexyl butyrate | 0.00% | methyl-eugenol | 0.00% |
| cis-ocimene | 0.00% | alpha-terpineol | 0.01-0.07% | Total Terpenes | 1.22-2.61% |
| trans-ocimene | 0.00-0.04% | citronellol | 0.00-0.01% | | |

The *cannabis* plant named 'CAKE BATTER COOKIES' has a complement of terpenes, including but not limited to, relatively high levels of limonene, beta-caryophyllene, beta-pinene, linalool, alpha-humulene, alpha-pinene, fenchol, myrcene, alpha-bisabolol, and alpha-terpineol compared to other terpene compounds. This unique combination of differently concentrated terpenes further distinguishes 'CAKE BATTER COOKIES' from other varieties in its odor, its medical qualities, and its effects on mood and mentation.

Asexual Reproduction

Asexual reproduction, also known as "cloning", is a process well known to those of ordinary skill in the art of *cannabis* production and breeding and includes the following steps.

The *cannabis* cultivar disclosed herein is asexually propagated via taking cuttings of shoots and putting them in rock wool cubes. These cubes are presoaked with pH adjusted water and kept warm (~80° F.). Full trays are covered, left under 18 hours of light and allowed to root (7-14 days). Upon root onset, the plantlets are transplanted into rigid 1 gallon containers filled with a proprietary soil mix A and remain in 18 hours of daylight for another 14-21 days. Once root-bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and the plant is dismantled to result in approximately 12" branches covered in inflorescences and trichomes. The goal in harvesting is to actually harvest trichome heads but not 'buds'. Thus, great care is taken not to disturb the trichome heads and as much of the plant remains intact as possible to promote even and slow drying. Slow drying is followed by a one to two months curing process.

Observation of the all female progenies of the original plant has demonstrated that this new and distinct cultivar has fulfilled the objectives and that its distinctive characteristics are firmly fixed and hold true from generation to generation vegetatively propagated from the original plant.

Under careful observation, the unique characteristics of the new cultivar have been uniform, stable and reproduced true to type in successive generations of asexual reproduction.

DESCRIPTION OF THE DRAWINGS

The accompanying color photographs depict characteristics of the new 'CAKE BATTER COOKIES' plants as nearly true as possible to make color reproductions. The overall appearance of the 'CAKE BATTER COOKIES' plants in photographs is shown in colors that may differ slightly from the color values described in the detailed botanical description.

DETAILED BOTANICAL DESCRIPTION

Figure 1:
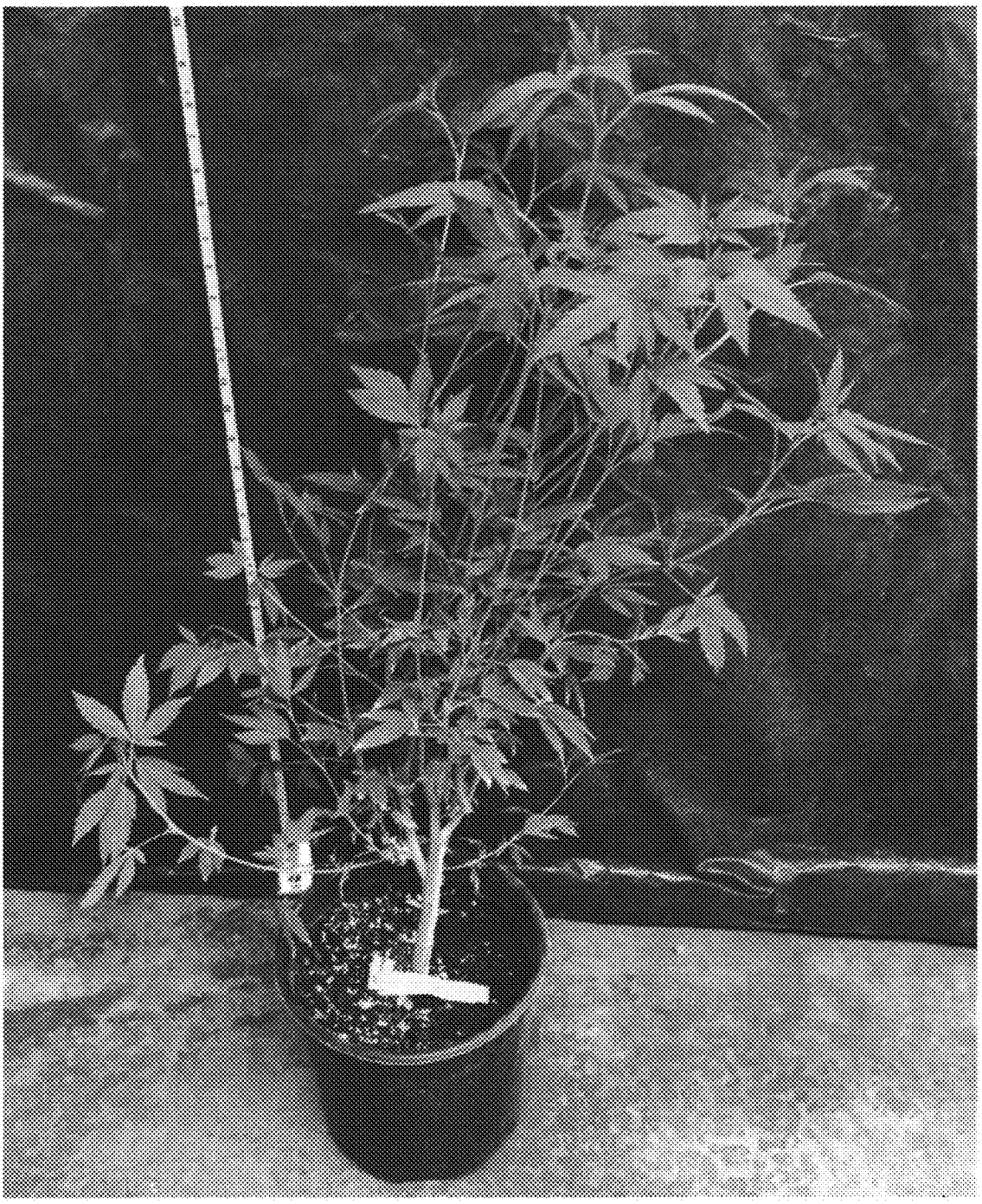
FIG. 1 shows an overall view of the 'CAKE BATTER COOKIES' plant from the side.
Figure 2A:
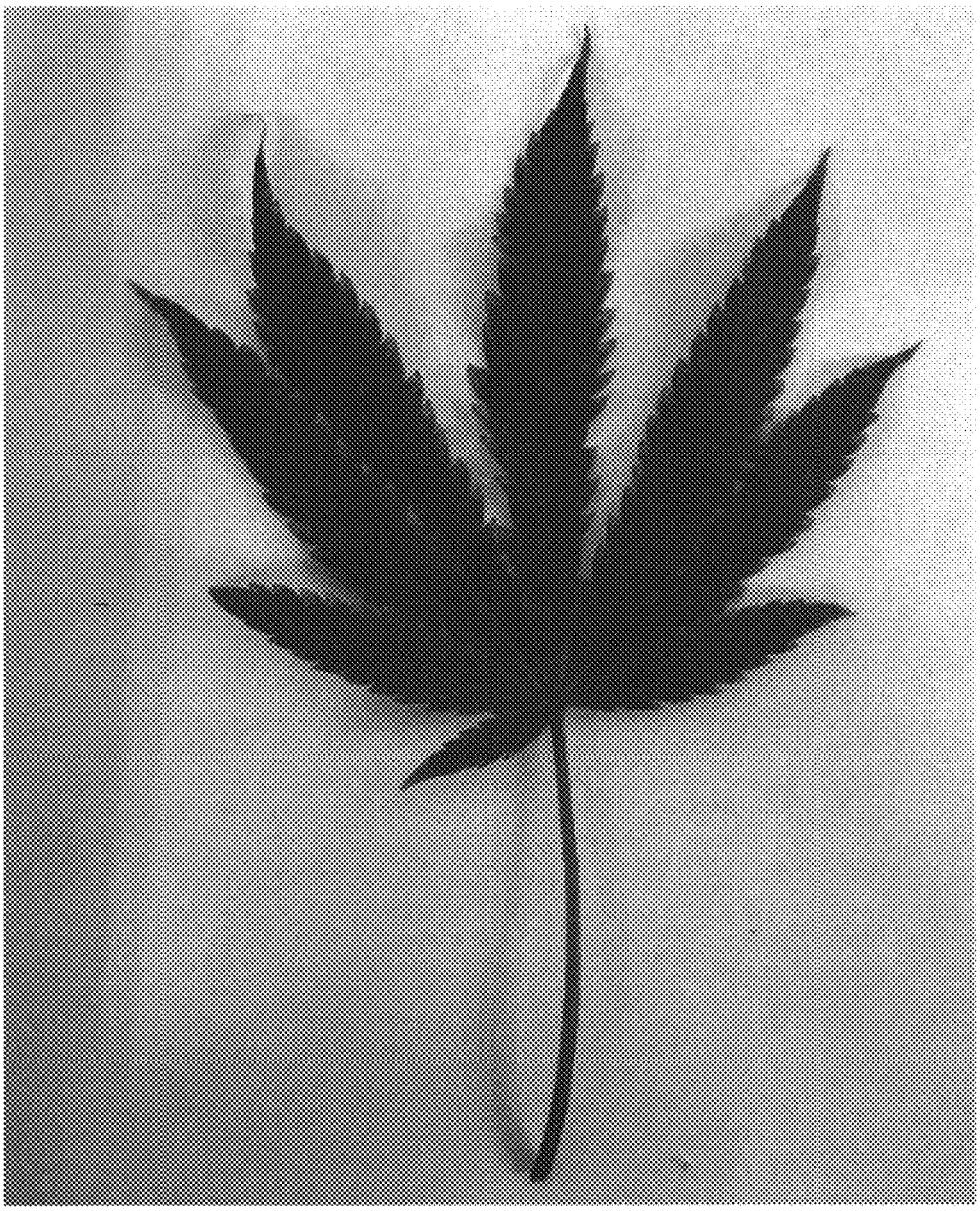
FIG. 2A shows a close view of a single leaf of the check variety BLK03 plant.
Figure 2B:
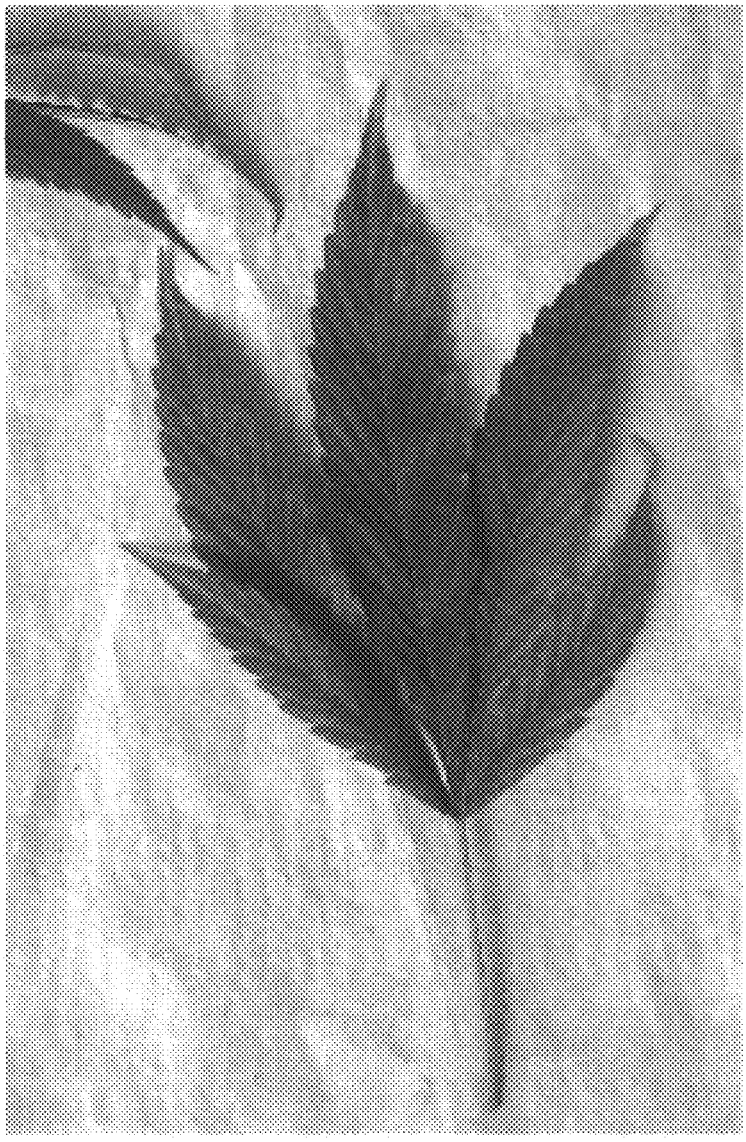
FIG. 2B shows a close view of a single leaf of the new variety 'CAKE BATTER COOKIES' plant.
Figure 3A:
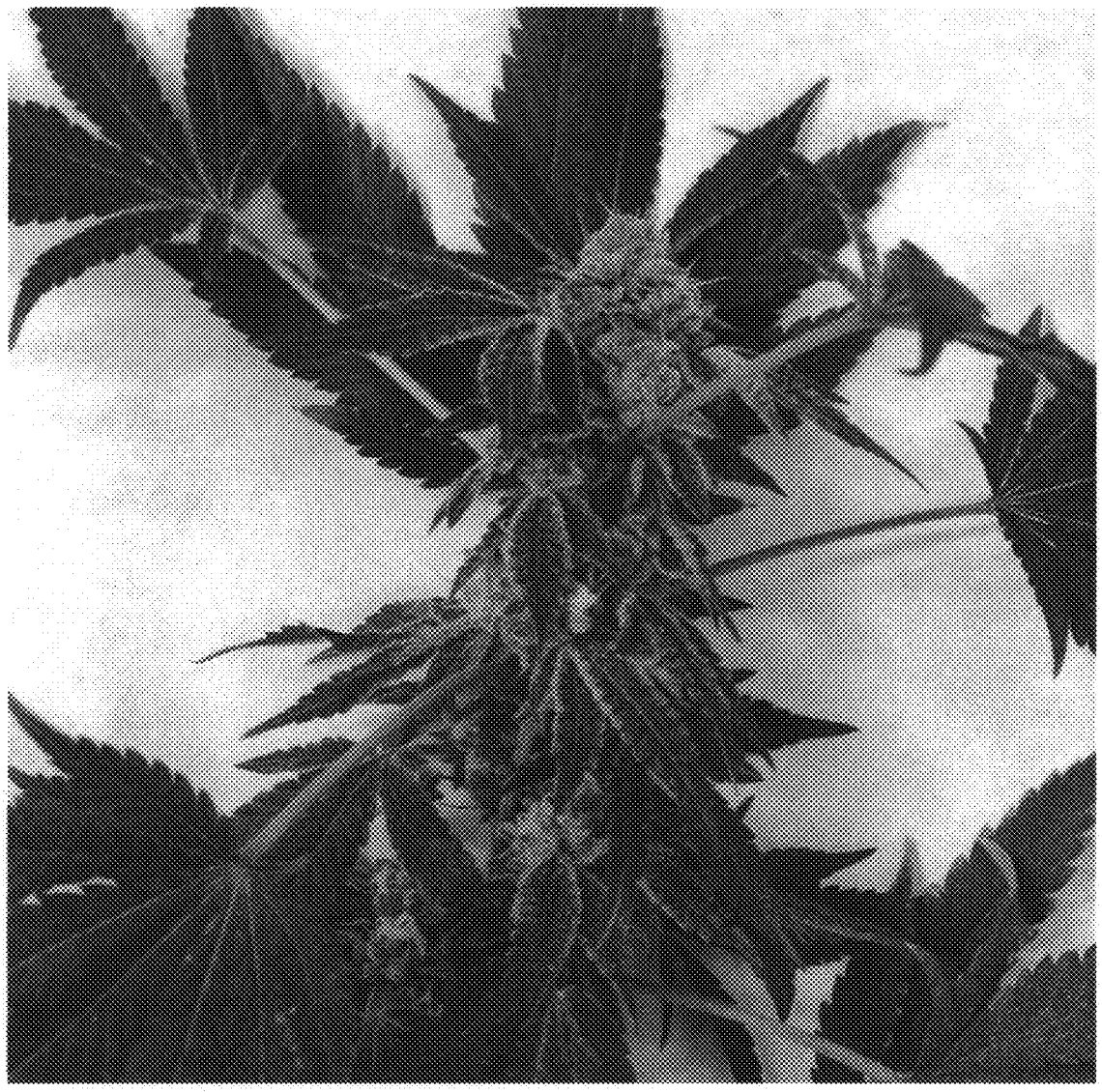
FIG. 3A shows top parts (including inflorescence) of the BLK03 plant from the side.
Figure 3B:
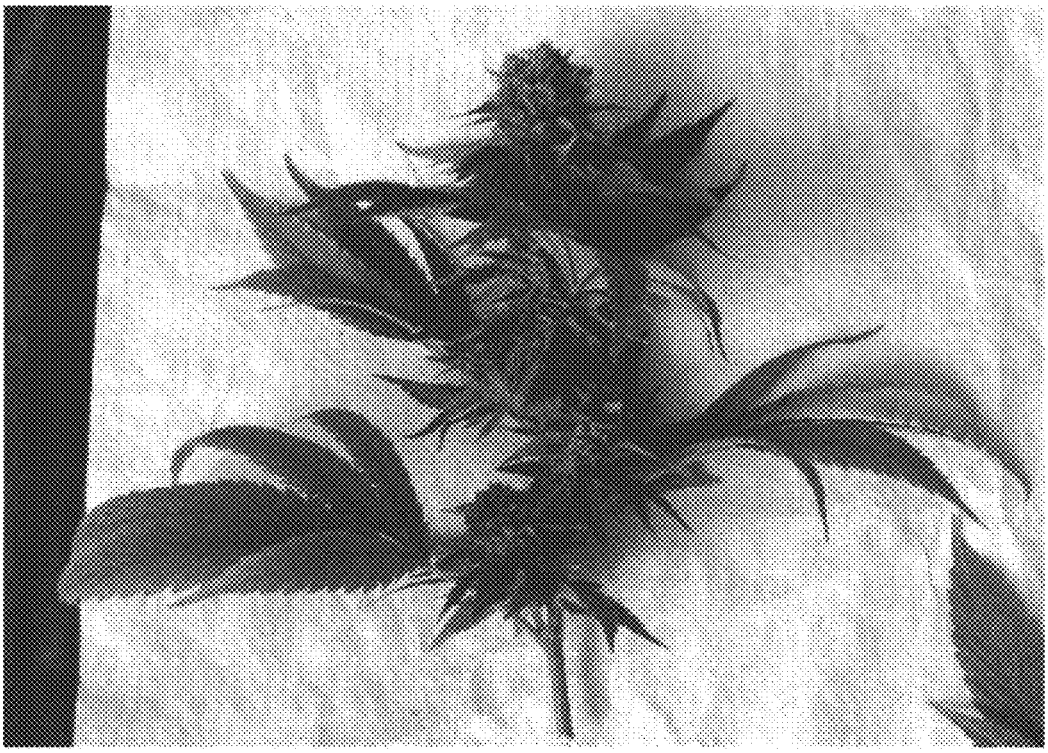
FIG. 3B shows top parts (including inflorescence) of the 'CAKE BATTER COOKIES' plant from the side.
Figure 4:
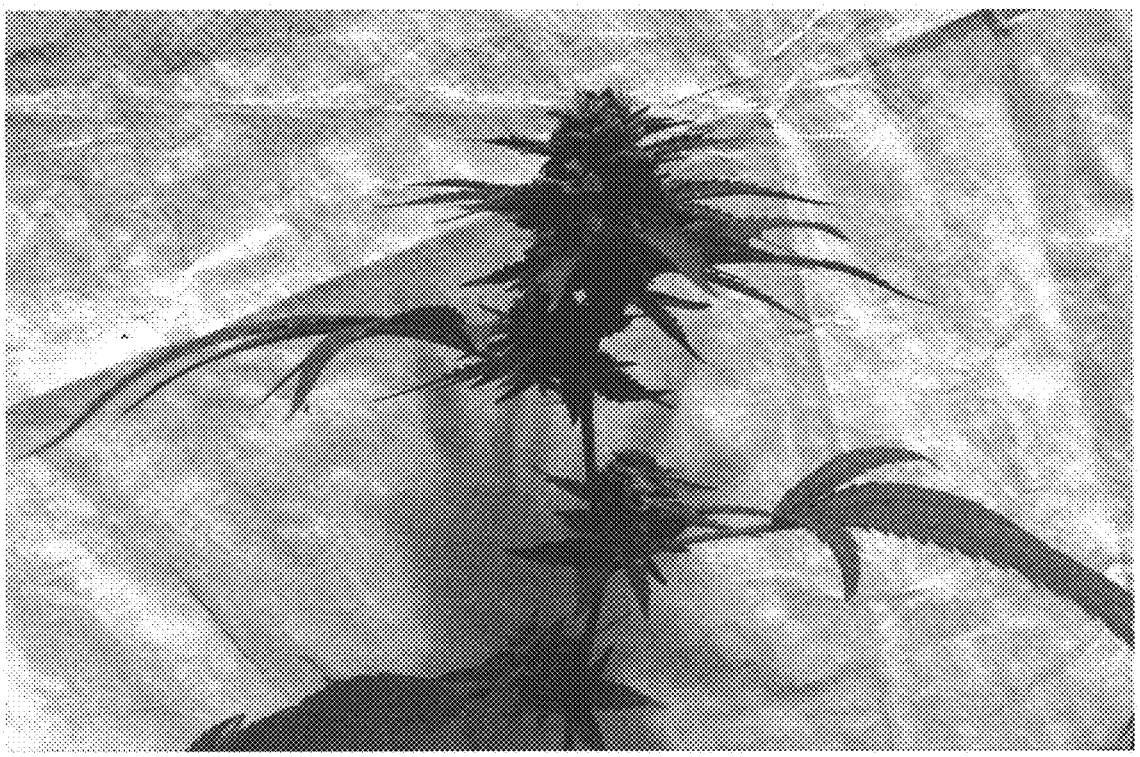
FIG. 4 shows another view of top parts (including inflorescence) of the 'CAKE BATTER COOKIES' plant from the side.
Figure 5:
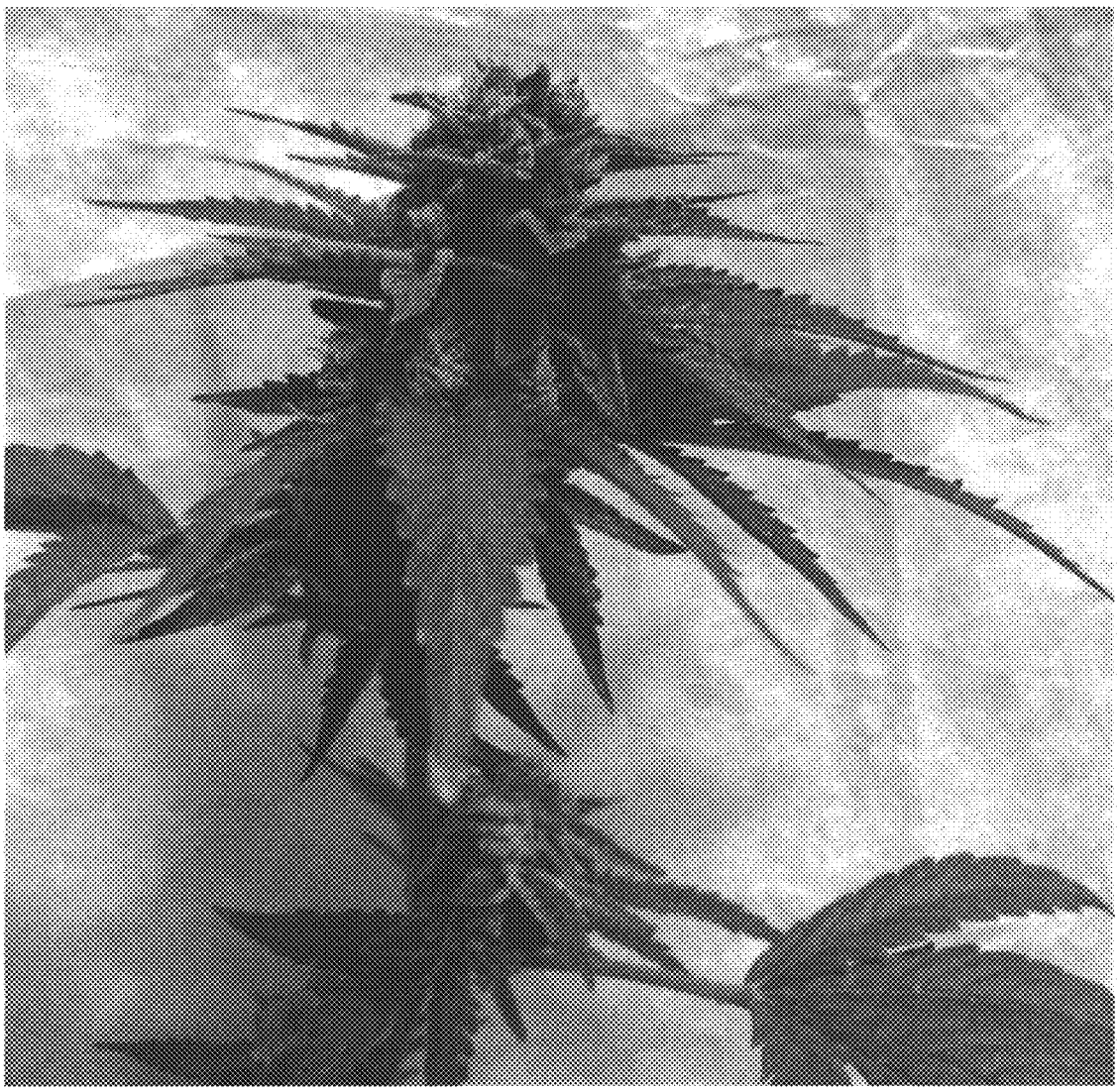
FIG. 5 shows a close view of flowers of the 'CAKE BATTER COOKIES' plant at the mid flowering stage.
Figure 6:
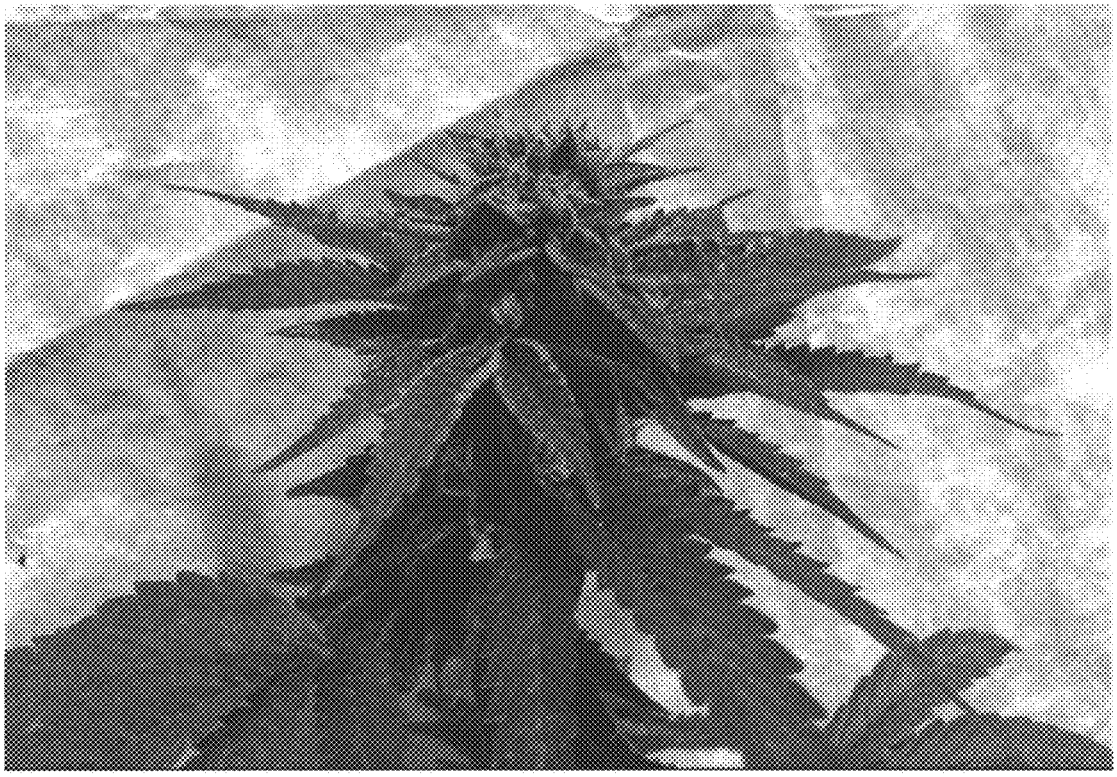
FIG. 6 shows another close view of flowers of the 'CAKE BATTER COOKIES' plant at the mid flowering stage.

'CAKE BATTER COOKIES' has not been observed under all possible environmental conditions, and the phenotype may vary significantly with variations in environment. The following observations, measurements, and comparisons describe this plant as grown at Salinas, Calif., when grown in the greenhouse, nursery or field, unless otherwise noted.

Plants for the botanical measurements in the present application are annual plants. In the following description, the color determination is in accordance with The Royal Horticultural Society Colour Chart, 2007 Edition, except where general color terms of ordinary dictionary significance are used.

The *cannabis* plant disclosed herein was derived, from female and male parents that are internally designated as below.

A GNBR internal Code of the *cannabis* plant named 'CAKE BATTER COOKIES' is K1.20.17. The variety name of 'CAKE BATTER COOKIES' is P08.BX.K1 x 16.81.20.17. 'CAKE BATTER COOKIES' is a fertile hybrid derived from a controlled-cross between two proprietary cultivars; (i) P08.BX.K1 (pollen acceptor; female parent) also known as K1 and (ii) P08.S1.16xP08.S1.81.20 (pollen donor; male parent) also known as 1681.20. A GNBR Breeding Code of 'CAKE BATTER COOKIES' is (P08.BX.K1)x(P08.S1.16xP08.S1.81.20).17. The additional number '.17' was only assigned to an individual plant (i.e. 'CAKE BATTER COOKIES') selected from hybrid progenies of the cross event between pollen acceptor (P08.BX.K1) and pollen donor (P08.S1.16xP08.S1.81.20). The initial cross between two parental cultivars was made in April 2016. The phenotypic criteria to select a new and distinct *cannabis* cultivar disclosed herein is as follows: structure score, nose/organoleptic, mold susceptibility/resistance, and insect susceptibility/resistance. Also, the first asexual propagation of 'CAKE BATTER COOKIES' occurred on Feb. 10, 2017 in Salinas, Calif.

The following traits in combination further distinguish the *cannabis* cultivar 'CAKE BATTER COOKIES' from the check variety 'BLK03', which is set as a standard for phenotypic comparison. Tables 2 to 6 present phenotypic traits and/or characteristics of 'CAKE BATTER COOKIES' compared to the check variety 'BLK03' as follows. All plants were raised together and evaluated when 100 days old (i.e., 25 days in vegetative stage, 15 days in propagation stage, and 60 days in flowering times).

TABLE 2

General Characteristics

| Characteristics | New Variety | Check Variety (BLK03) |
|---|---|---|
| Plant life forms | An herbaceous plant (herb) | An herbaceous plant (herb) |
| Plant growth habit | An upright, tap-rooted annual plant; forming fibrous roots when asexually propagated | An upright, tap-rooted annual plant; forming fibrous roots when asexually propagated |
| Plant origin | A controlled-cross between pollen acceptor (P08.BX.K1) and pollen donor (P08.S1.16 × P08.S1.81.20) | A controlled-cross between pollen acceptor (GLD13) and pollen donor (BSIA) |
| Plant propagation | Asexually propagated by cuttings and cloning | Asexually propagated by cuttings and cloning |
| Propagation ease | Moderate | Moderate |
| Height | 1.5-2.5 m | 0.5-2.5 m |
| Width | 162 cm | 119.5 cm |
| Plant vigor | High | Medium |
| Time to Harvest (Seed to Harvest) | 11 weeks | 8 weeks |
| Resistance to pests or diseases | Resistant to pest as follows; (1) two-spotted spider mite (*Tetranychus urticae*) (Koch); (2) Aphids species such as: Cannabis Aphids (*Phorodon cannabis*), Green Peach Aphid (*Myzus persicae*) (Sulzer), Foxglove Aphid (*Aulacorthum solani*), Peach Aphid (*Macrosiphum euphorbiae*), Black Bean Aphid (*Aphis fabae*); (3) Whitefly (*Trialeurodes vaporariorum*; (4) Lepidoptera species such as: Armyworm (*Spodoptera frugiperda*), Cabbage Whites (*Pieris rapae*), Painted Lady (*Vanessa cardui*), Lepidoptera sp.; (5) Leaf Miner (*Liriomyza sativae*) Resistant to diseases as follows; Botrytis/Flower Rot (*Botrytis* cinerea), Powdery Mildew (*Podosphaera xanthii*) | Non-Resistant to two spotted spider mite or aphids, white-fly, but resistant to Lepidoptera species |
| Genetically-modified organism | NO | NO |

TABLE 3

Leaf/Foliage

| Characteristics | New Variety | Check Variety (BLK03) |
|---|---|---|
| Leaf arrangement | Alternate | Alternate |
| Leaf shape | Palmately compound with overlapping leaflets | Palmately compound |
| Leaf structure | Linear-lanceolate leaflet blades with glandular hairs | Linear-lanceolate leaflet blades with glandular hairs |

TABLE 3-continued

Leaf/Foliage

| Characteristics | New Variety | Check Variety (BLK03) |
|---|---|---|
| Leaf margins | Dentate, coarsely serrated. and the teeth point away from the tip | Dentate, coarsely serrated, and the teeth point away from the tip |
| Leaf hairs | Present on both upper and lower surfaces | Present on both upper and lower surfaces |
| Leaf length with petiole at maturity | 27.9 cm | 16.6 cm |
| Leaf width at maturity | 10.6-18.3 cm | 10.7 cm |
| Petiole length at maturity | 8.8 cm | 6.5 cm |
| Petiole color (RHS No.) | 150D | 140C |
| Intensity of petiole anthocyanin | Medium (early on in vegetative growth); strong (during flower maturation) | Medium (vegetative stage); very strong (late flowering stage) |
| Stipule length at maturity | 0.8 cm | 0.7 cm |
| Stipule shape | Elliptical | Elliptical |
| Stipule color (RHS No.) | 134B | 149B |
| No. of leaflets | 5-7 | 5-7 |
| Middle largest (longest) leaflet length | 19.7 cm | 9.8 cm |
| Middle largest (longest) leaflet width | 4.2 cm | 2.3 cm |
| Middle largest (longest) leaflet length/width ratio | 19.7:4.2 | 9.8:2.3 |
| No. teeth of middle leaflet (average) | 33 | 25 |
| Leaf (upper side) color (RHS No.) | 132B | 132A |
| Leaf (lower side) color (RHS No.) | 134C | 134D |
| Leaf glossiness | Moderate | Strong |
| Vein/midrib shape | Obliquely continuous throughout leaflet | Obliquely continuous throughout leaflet |
| Vein/midrib color | N144C | 144C |
| Aroma | Floral, lavender | Spicy |

TABLE 4

Stem

| Characteristics | New Variety | Check Variety (BLK03) |
|---|---|---|
| Stem shape | Hollow, ribbed, large | Hollow, ribbed, textured |
| Stem diameter at base | 5.5 cm | 2.8 cm |
| Stem color (RHS No.) | 150D | N144D |
| Depth of main stem ribs/grooves | Medium | Absent |
| Internode length | 5.7-14.2 cm | 2.4-4.9 cm |

TABLE 5

| Inflorescence (Female/Pistillate Flowers) | | |
|---|---|---|
| Characteristics | New Variety | Check Variety (BLK03) |
| Flowering (blooming) habit | Elongated compound cymes, from 0.5 m-1.5 m in length | Elongated compound cymes, from 0.5 m-1.2 m in length |
| Proportion of female plants | 100% pistillate | 100% pistillate |
| Inflorescence position | Above | Even |
| Flower arrangement thereafter) | Cymose | Cymose (terminal bud matures, while lateral flowers mature |
| Number of flowers per plant | 85-130 per cyme | 80-120 per cyme |
| Flower shape | Calcarate-urceolate | Calcarate-urceolate |
| Flower (individual pistillate) length | 0.7 cm | 0.7 cm |
| Flower (compound cyme) diameter | 4.9 cm | 3.8 cm |
| Corolla size | 0.12-0.48 cm | 0.08-0.25 cm |
| Corolla Color (RHS No.) | n/a | n/a |
| Bract shape | Urceolate | Urceolate |
| Bract size | 0.1-0.8 cm | 0.2-0.8 cm |
| Bract color (RHS No.) | 134B | N134C |
| Calyx shape | No defined calyx | No defined calyx |
| Calyx color (RHS No.) | n/a | n/a |
| Stigma shape | Acute and Round | Acute |
| Stigma length | 3.0 mm | 2.2 mm |
| Stigma color (RHS No.) | 42C | 159D |
| Trichome shape | Capitate-stalked glandular | Capitate-stalked |
| Trichome color (RHS No.) | 157A before harvest, at approximately day 40 of flowering | glandular 157A at day 40 in flowering |
| Other types of trichomes | Capitate sessile trichomes are present on the leaves of plants, as well as being noticed in the flowers(color: 157A at day 45 in flowering).<br><br>During later flowering, i.e. day 50 to day 70 in flowering, the capitate stalked trichomes are present (color: N30B).<br><br>Bulbous and non-glandular trichomes are also present and most noticeable on the petioles, stems, and leaves (color: 157A). | Capitate sessile trichomes are present on the leaves of plants, as well as being noticed in the flowers (color: 157A at day 40 in flowering). During later flowering, i.e. day 48 to day 60 in flowering, capitate stalked trichomes are present (color: N30B). |
| Terminal bud shape | Oblong | Oblong |
| Terminal bud color (RHS No.) | 131C | 203C |
| Pedicel | Absent | Absent |
| Staminate shape | No staminate flowers produced naturally; however, male flower (staminate) can be induced with chemical compounds (such as silver nitrate and silver thiosulphate anionic complex). | No staminate flowers produced naturally; however, male flower (staminate) can be induced with chemical compounds (such as silver nitrate and silver thiosulphate anionic complex). |
| Pollen description | Absent | Absent |
| Seed shape | Smooth and globular | Smooth and globular |
| Seed size/length | 1.8-2.4 mm | 1.8-2.3 mm |

TABLE 5-continued

| Inflorescence (Female/Pistillate Flowers) | | |
|---|---|---|
| Characteristics | New Variety | Check Variety (BLK03) |
| Marbling of seed | Weak; absent (some seeds) | Absent (non-existent) |
| Petal description | Apetalous | Apetalous |
| Max THC content | About 6.50-14.21% | About 18.88-19.37% |
| Max CBD content | About 5.36-9.82% | 0.00% |
| Max CBG content | About 0.11-0.42% | About 0.84-0.91% |

n/a: not available

TABLE 6

| Other Characteristics | | |
|---|---|---|
| Characteristics | New Variety | Check Variety (BLK03) |
| Time period and condition of flowering/blooming | 8-10 weeks | 7-9 weeks |
| Hardiness of plant | Hardy to 25° F.-ambient temperature | Hardy to 25° F.-ambient temperature |
| Breaking action | Flexible, highly resistant tobreakage | Strong, non-flexible |
| Rooting rate after cutting/cloning | 99%-vigorous | 70%-moderate |
| Types of Cutting for Cloning | Stem | Stem |
| Shipping quality if available | High | Moderate |
| Storage life if available | Long (6-9 months with minor changes in physical appearance and/or smell/taste); minor decrease in green coloration | Medium (2-6 months with minor changes in physical appearance and/or smell/taste) |
| Market use | Medicinal | n/a |
| Productivity of flower if available | Approximately 0.227-1.134 kg can be produced per plant, dependent on finished plant size (1.3-3.2 m); Growing conditions/environment will dictate final yield/output | Approximately 0.14-0.45 kg can be produced per plant; dependent on finished size (0.6-1.2 m); Growing conditions/environment will dictate final yield/output |

n/a: not available

In general, 'CAKE BATTER COOKIES' is larger in height than both parents, K1 (a.k.a P08.BX.K1) and 1681.20 (a.k.a P08.S1.16xP08.S1.81.20). 'CAKE BATTER COOKIES' is more robust in terms of growing performance, time to rooted clones, and time to flower maturity. Also, 'CAKE BATTER COOKIES' has greater resistance to pest and disease, stronger branches, thicker stems, greater flexibility, and higher yielding. 'CAKE BATTER COOKIES' clearly demonstrates hybrid vigor, and outperforms both parents overall. Chemically, 'CAKE BATTER COOKIES' has a higher cannabinoid content, a higher THC:CBD ratio as well as a higher terpene content than either parent.

When 'CAKE BATTER COOKIES' is compared to the check variety 'BLK03', 'CAKE BATTER COOKIES' is wider than 'BLK03' in plant width. 'CAKE BATTER COOKIES' shows higher plant vigor than 'BLK03'. In general, 'CAKE BATTER COOKIES' has a longer leaf length including petiole than 'BLK03'. Also, 'CAKE BATTER COOKIES' has longer and wider leaflets than 'BLK03' when comparing the middle largest leaflet length and width. Additionally, 'CAKE BATTER COOKIES' has more teeth numbers in middle leaflet than 'BLK03'. Regarding the petiole length, 'CAKE BATTER COOKIES' is longer than 'BLK03' at maturity. Regarding stem diameter at base, 'CAKE BATTER COOKIES' is longer than 'BLK03'. When comparing the compound cyme diameter, 'CAKE BATTER COOKIES' is also longer than 'BLK03'. With respect to aroma, 'CAKE BATTER COOKIES' have a floral lavender odor, while 'BLK03' has a generally spicy odor.

When 'CAKE BATTER COOKIES' is compared to the known *cannabis* plant named 'ECUADORIAN SATIVA' (U.S. Pat. No. 27,475), there are several distinctive characteristics. For example, overall form of 'CAKE BATTER COOKIES' plant is wider than the 'ECUADORIAN SATIVA' plant at the widest point. 'CAKE BATTER COOKIES' plant has a longer middle leaflet (without petiole) and whole leaf (with petiole) length than the 'ECUADORIAN SATIVA' plant. Also, 'CAKE BATTER COOKIES' plant has a wider middle leaflet and whole leaf width than the 'ECUADORIAN SATIVA' plant. Regarding stem diameter at base, 'CAKE BATTER COOKIES' is longer than 'ECUADORIAN SATIVA'. While the aroma of 'ECUADORIAN SATIVA' is strongly mephitic with hints of limonene, 'CAKE BATTER COOKIES' has a floral lavender smell. When comparing total THC content between 'CAKE BATTER COOKIES' and 'ECUADORIAN SATIVA', the total THC content of 'CAKE BATTER COOKIES' is between 6.50-14.21%, while 'ECUADORIAN SATIVA' accumulates 12.45% total THC.

The invention claimed is:

1. A new and distinct cultivar of *Cannabis* plant named 'CAKE BATTER COOKIES' substantially as shown and described herein.

* * * * *

CAKE BATTER COOKIES

BLK03

CAKE BATTER COOKIES

BLK03

CAKE BATTER COOKIES

CAKE BATTER COOKIES

CAKE BATTER COOKIES

CAKE BATTER COOKIES